(12) United States Patent
Moriyama

(10) Patent No.: US 7,238,153 B2
(45) Date of Patent: Jul. 3, 2007

(54) ENDOSCOPE HOOD

(75) Inventor: Hiroki Moriyama, Akishima (JP)

(73) Assignee: Olympus Corporation (JP)

( * ) Notice: Subject to any disclaimer, the term of this patent is extended or adjusted under 35 U.S.C. 154(b) by 81 days.

(21) Appl. No.: 10/682,060

(22) Filed: Oct. 9, 2003

(65) Prior Publication Data

US 2004/0077928 A1    Apr. 22, 2004

Related U.S. Application Data

(63) Continuation of application No. PCT/JP03/04432, filed on Apr. 8, 2003.

(30) Foreign Application Priority Data

Apr. 8, 2002    (JP) ............................. 2002-105348

(51) Int. Cl.
*A61B 1/00*    (2006.01)
(52) U.S. Cl. ........................ 600/127; 600/128; 600/129
(58) Field of Classification Search ................ 600/121, 600/127, 129, 104
See application file for complete search history.

(56) References Cited

U.S. PATENT DOCUMENTS

| | | | | |
|---|---|---|---|---|
| 4,825,259 | A * | 4/1989 | Berry, Jr. ................. | 356/241.4 |
| 5,002,042 | A | 3/1991 | Okada ............................ | 128/6 |
| 5,897,487 | A * | 4/1999 | Ouchi ......................... | 600/127 |
| 6,855,108 | B2 * | 2/2005 | Ishibiki et al. ............... | 600/127 |
| 6,916,284 | B2 * | 7/2005 | Moriyama ................... | 600/127 |
| 2002/0035311 | A1 | 3/2002 | Ouchi ......................... | 600/156 |
| 2004/0260149 | A1 * | 12/2004 | Ishibiki ....................... | 600/127 |
| 2004/0267092 | A1 * | 12/2004 | Ishibiki ....................... | 600/127 |

FOREIGN PATENT DOCUMENTS

| | | |
|---|---|---|
| JP | 8-89474 | 4/1996 |
| JP | 11-313795 | 11/1999 |
| JP | 2001-224550 | 8/2001 |
| JP | 2001-275933 | 10/2001 |
| JP | 2002-95623 | 4/2002 |
| JP | 2003-116772 | 4/2003 |

OTHER PUBLICATIONS

European Search Report dated Jul. 21, 2005.

(Continued)

*Primary Examiner*—Linda C. M. Dvorak
*Assistant Examiner*—Matthew J. Kasztejna
(74) *Attorney, Agent, or Firm*—Ostrolenk, Faber, Gerb & Soffen, LLP

(57) ABSTRACT

An endoscope hood has a protrusion portion which protrudes in an observation visual field direction of an endoscope at an end of a cylindrical press fitting fixing portion attached by press fitting in a state that an attachment position in a circumferential direction is positioned at a distal end portion of an endoscope insertion portion in an appropriate direction. Further, there is provided attachment state confirming device which increases an area of the protrusion portion displayed in an endoscope observation image when the press fitting fixing portion is attached to a distal end portion of a second endoscope insertion portion having a size different from that of a first endoscope insertion portion to which the press fitting fixing portion can be appropriately attached, and gives a warning about an inappropriate attachment state.

23 Claims, 5 Drawing Sheets

OTHER PUBLICATIONS

Search Report prepared by European Patent Office on Jul. 21, 2005 in connection with corresponding European patent application No. 03 715 782.3.

Letter from Spanish associate dated Jul. 29, 2005 forwarding Search Report to Japanese associate, stating relevancy of disclosed art to corresponding European application.

English Abstract prepared by Patent Abstracts of Japan for Japanese patent application No. JP 2002-95623 cited in Search Report.

International Search Report.

Information Disclosure Sheet under Rule 1.56.

Untranslated Office Action issued by Chinese Patent Office on Sep. 8, 2006 in connection with corresponding patent application No. 038013266.

English translation of Chinese Office Action submitted in lieu of statement of relevancy of prior art to present invention.

English translation of International Search Report dated Apr. 24, 2003 in relation to PCT/JP03/04432.

* cited by examiner

ENDOSCOPE HOOD

CROSS-REFERENCE TO RELATED APPLICATIONS

This is a Continuation Application of PCT Application No. PCT/JP03/04432, filed Apr. 8, 2003, which was not published under PCT Article 21(2) in English.

This application is based upon and claims the benefit of priority from the prior Japanese Patent Application No. 2002-105348, filed Apr. 8, 2002, the entire contents of which are incorporated herein by reference.

BACKGROUND OF THE INVENTION

1. Field of the Invention

The present invention relates to an endoscope hood which is attached to a distal end portion of an endoscope insertion portion by press fitting.

2. Description of the Related Art

In order to facilitate focusing of an endoscope observation image and stable observation, observation may be carried out with a cylindrical endoscope hood being attached to a distal end portion of an endoscope insertion portion.

As such a hood, for example, Jpn. Pat. Appln. KOKAI Publication No. 2001-224550 discloses a technique which prevents a protrusion portion which protrudes in an observation visual field direction on a distal end of a hood main body from being displayed on an endoscope observation image. The hood according to this technique has at least a part of the protrusion portion formed into an angular shape along an outer edge of an observation visual field or a shape that an end is partially cut so as to prevent an observation visual field from being obscured.

The endoscope hood has a hood main body formed of a soft material such as a rubber. Such a hood is fixed by elastically deforming the cylindrical hood main body and press-fitting a fitting hole portion of the hood main body to a distal end portion of the endoscope insertion portion. Therefore, it is possible to attach a hood with a size other than an appropriate size such that an inside diametric dimension of the fitting hole portion (inner peripheral surface) of the hood main body fitted onto the distal end portion of the endoscope insertion portion is set to an appropriate dimension with respect to an outside diametric dimension of the distal end portion of the insertion. For example, even if an outside diameter of the distal end portion of the insertion portion to which the hood is attached is too large or too small with respect to a standard dimension, since the material of the hood is elastically deformed, the hood can be attached to the distal end portion of the endoscope insertion portion.

BRIEF SUMMARY OF THE INVENTION

The endoscope hood has: a cylindrical attachment portion which can be attached to a distal end portion of an insertion portion of a second endoscope which has an outside diameter appropriate to attachment to a predetermined position, which can be attached to a distal end portion of an insertion portion of a first endoscope, has an outside diameter different from that of the distal end portion of the insertion portion of the first endoscope; and a protrusion portion which is formed on an end side of this attachment portion, protrudes from distal end portions of the insertion portions of the first and second endoscopes in an observation visual field direction, and has an area displayed in an observation image of the second endoscope larger than an area displayed in an observation image of the first endoscope.

DETAILED DESCRIPTION OF THE INVENTION

Figure 1:
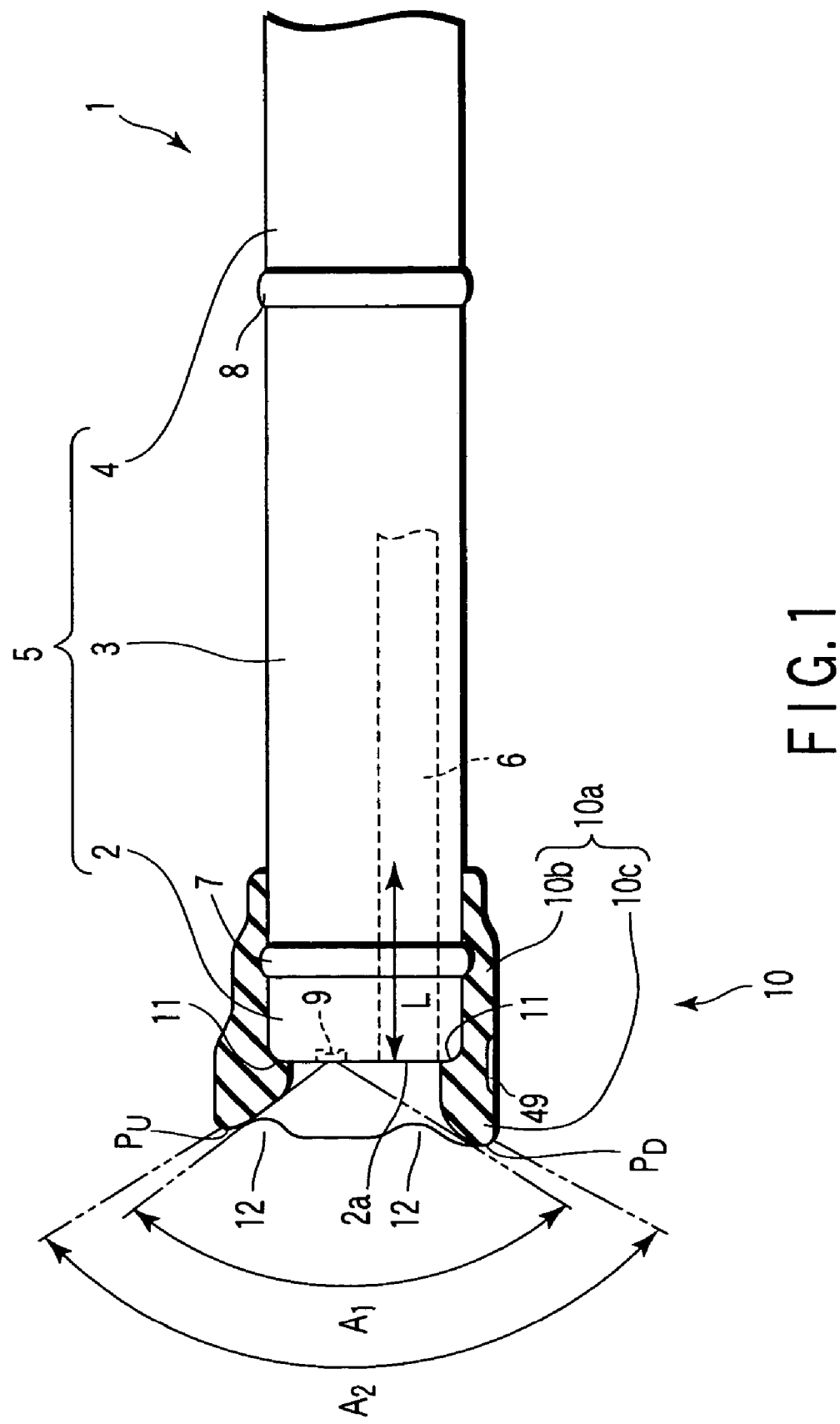
FIG. 1 is a schematic partial cross-sectional view showing a state that a hood according to an embodiment of the present invention is attached to an endoscope distal end portion.
Figure 2:
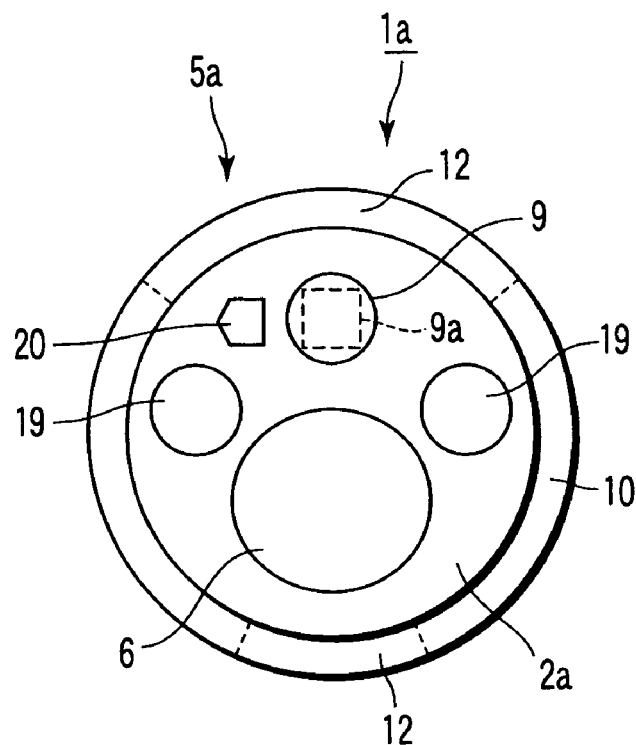
FIG. 2 is a schematic front view showing the endoscope distal end portion with the hood according to the embodiment of the present invention attached thereto from a distal end direction.

FIG. 1 shows a distal end part of a direct vision type endoscope 1 which views in a front direction. Furthermore, FIG. 2 shows an end part of an endoscope (which may be referred to as a first endoscope 1a hereinafter) when a later-described hood 10 having an appropriate size relative to the endoscope 1 depicted in FIG. 1 is attached. It is to be noted that a later-described insertion portion 5a of the first endoscope 1a has the same structure as a later-described insertion portion 5. It is determined that insertion portions 5b and 5c of later-described second and third endoscopes 1b and 1c are different in arrangement position but have the same constituent elements as those of the insertion portion 5 for the sake of convenience.

As shown in FIG. 1, the insertion portion 5 of the endoscope 1 includes a hard distal end portion 2, a bendable bending portion 3 connected to a proximal end portion of the distal end portion 2, and a soft portion 4 which is connected to a proximal end portion of this bending portion 3 and has the flexibility in the mentioned order from the end side. An end surface of the distal end portion 2, i.e., a distal end surface 2a of the insertion portion 5 is formed flat so as to be orthogonal to an axial direction of the distal end portion 2. The distal end portion 2 and the bending portion 3 are connected to each other through a ring-shaped first connection portion 7, and the bending portion 3 and the soft portion 4 are likewise connected to each other through a ring-shaped second connection portion 8.

In such an insertion portion 5 are inserted, e.g., a endo-therapy accessory channel 6 indicated by a broken line in FIG. 1, an illumination optical system, an observation optical system, and a plurality of elements such as an air supply/water supply path. Various kinds of endo-therapy accessories such as a grasping forceps are inserted into the endo-therapy accessory channel 6. The illumination optical system guides a light ray from a light source device (not shown) on the proximal end portion side of the insertion portion and leads it to the distal end portion of the endoscope 1. The observation optical system is used to observe an analyte, which is illuminated by the illumination optical system, at the distal end portion 2a of the insertion portion 5 of the endoscope 1. An observation image at the distal end portion 2a is displayed in an observation image display portion 14 provided to the monitor device 13 which is connected to the proximal end portion side of the insertion portion 5 and shown in FIG. 3.

As shown in FIG. 2, on the distal end surface 2a of the distal end portion 2 of the first endoscope 1a, an opening portion of the endo-therapy accessory channel 6 which is generally the largest element on this distal end surface 2a is opened on the rather lower side away from the center of the distal end surface 2a. On this distal end surface 2a are provided a pair of illumination lenses 19 disposed at the end of the illumination optical system and a circular object lens 9 provided at the end of an object optical system. Each of the illumination lenses 19 is arranged in the right or left direction with respect to the center of the distal end surface 2a and on the upper side away from the endo-therapy accessory channel 6. The object lens 9 is arranged on the rather upper side with respect to the center. A mask 9a which assures a visual field area having a substantially square shape such as indicated by a broken line in FIG. 2 is applied on this object lens 9. That is, the circular object lens 9 has a circumference thereof being covered while the substantially square visual field area is assured at the center thereof.

As shown in FIG. 1, a field angle of this object lens 9 is A1 in an opposite side direction corresponding to the observation image display portion 14 of the monitor device 13, and it is A2 in a diagonal direction. Visible field areas of these field angles A1 and A2 are different from each other (A1<A2). Meanwhile, it is assumed that the maximum field angle A1 in the opposite side direction of the object lens 9 of this endoscope 1 (first endoscope 1a) is, e.g., 140°. A distance between the center of the object lens 9 and an outer peripheral portion of the distal end portion 2 is assumed to be, e.g., 3.2 mm.

Figure 3:
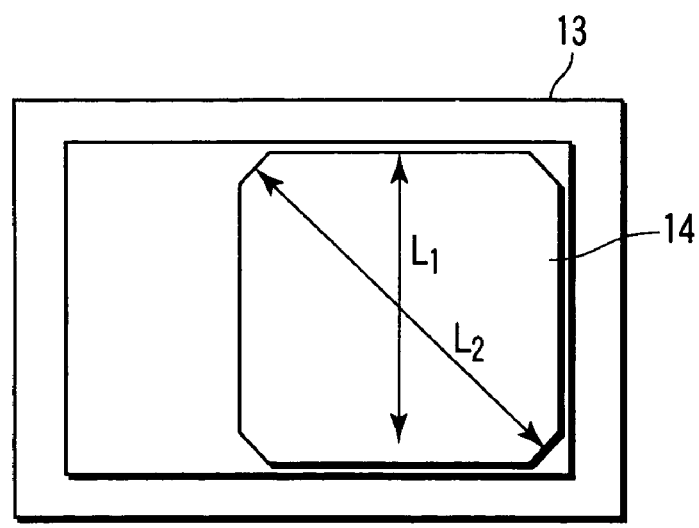
FIG. 3 is a schematic view showing a monitor device for an observation image from the endoscope distal end portion depicted in FIG. 1.

In the monitor device 13 shown in FIG. 3, the observation image display portion 14 obtained by the endoscope 1 is formed into a substantially rectangular shape such as a square shape by the above-described mask 9a. A visual field area of the object lens 9 displayed in this observation image display portion 14 has a shape that four corners of, e.g., a square shape are cut out. In regard to the visual field area of the observation image display portion 14, a length in the opposite side direction is L1 and a length in the diagonal direction that the four corners are cut out is L2, for example. These lengths L1 and L2 are different from each other (L1<L2).

It is preferable that an image-processing device (not shown) is attached to this monitor device 13, for example. It is preferable that this image-processing device can automatically apply, e.g., binarization processing to an image displayed in the later-described observation image display portion 14 of the monitor device 13 and calculate an area ratio of that processed image.

It is to be noted that an air supply/water supply nozzle 20 is connected to the above-described air supply/water supply path and caused to protrude on the distal end surface 2a as shown in FIG. 2. This air supply/water supply nozzle 20 blows off foreign particles and the like which have adhered to the object lens 9 or performs, e.g., cleansing of the object lens 9. FIG. 1 does not illustrate the air supply/water supply nozzle 20 in order to avoid complication of the drawing.

As shown in FIG. 1, the endoscope hood 10 is attached to the distal end portion 2 of the endoscope insertion portion 5 so as to appropriately maintain a focal distance between itself and, e.g., an object, and the endoscope 1 is used. This hood 10 is formed of an elastic body, e.g., rubber.

This hood 10 includes a cylindrical hood main body 10a. A cylindrical press fitting fixing portion (attachment portion) 10b which can be elastically deformed in the radial direction and a cylindrical protrusion portion (small-diameter portion) 10c which is integrally formed on the end side of this press fitting fixing portion 10b and protrudes from the distal end portion 2 of the insertion portion 5 of the endoscope 1 at the time of attachment are integrally formed to this hood main body 10a. The protrusion portion 10c has an inner peripheral surface, whose diameter is smaller than that of an inner peripheral surface (fitting hole portion) of the press fitting fixing portion 10b, on the proximal end portion thereof. A step is formed on the inside diameter of each inner peripheral surface of the press fitting fixing portion 10b and the proximal end portion of the protrusion portion 10c. This step functions as an impingement end portion 11 against which an outer edge portion of the distal end surface 2a of the distal end portion 2 of the endoscope insertion portion 5 is pressed. This impingement end portion 11 determines a position in the axial direction when the hood 10 is attached to the distal end portion 2 of the insertion portion 5 of the endoscope 1. It is preferable that the inside diameter of the inner peripheral surface of the press fitting fixing portion 10b on the rear end side away from this impingement end portion 11 is uniform, and its diametric length is d.

On the other hand, the protrusion portion 10c further protrudes to the front side from the distal end portion 2 of the endoscope insertion portion 5, and its end is brought into contact with, e.g., a living tissue. One or a plurality of concave portions 12 which prevent the inner peripheral surface (outer edge portion) of the protrusion portion 10c of the hood 10 from being displayed in the visible area of the object lens 9 are formed at the end of this protrusion portion 10c. In the hood main body 10a which can be attached to the endoscope 1 according to this embodiment, two concave portions 12 which are partially cut in, e.g., a circumferential direction are formed as shown in FIG. 2.

It is to be noted that since the visual field varies depending on a position of the distal end surface 2a at which the object lens 9 is arranged, a position of the concave portion 12 also varies depending on the arrangement of the object lens 9. A protrusion quantity of the protrusion portion 10c also varies depending on an observation visual field or a focal distance.

That is, the hood 10 according to this embodiment has the directivity with respect to the circumferential direction and the axial direction of the distal end portion 2 of the endoscope insertion portion 5.

As shown in FIG. 1, in order to avoid inhibition of bend of the bending portion 3, a longitudinal length of the insertion portion 5 that the hood 10 is pressure-welded fitted to the distal end portion 2 of the endoscope insertion portion 5 is formed to be shorter than a length L of the hard member from the distal end surface 2a of the distal end portion 2. That is, a length from the impingement end portion 11 of the hood 10 to the rear end is formed shorter than the length of the hard member.

Figure 4:
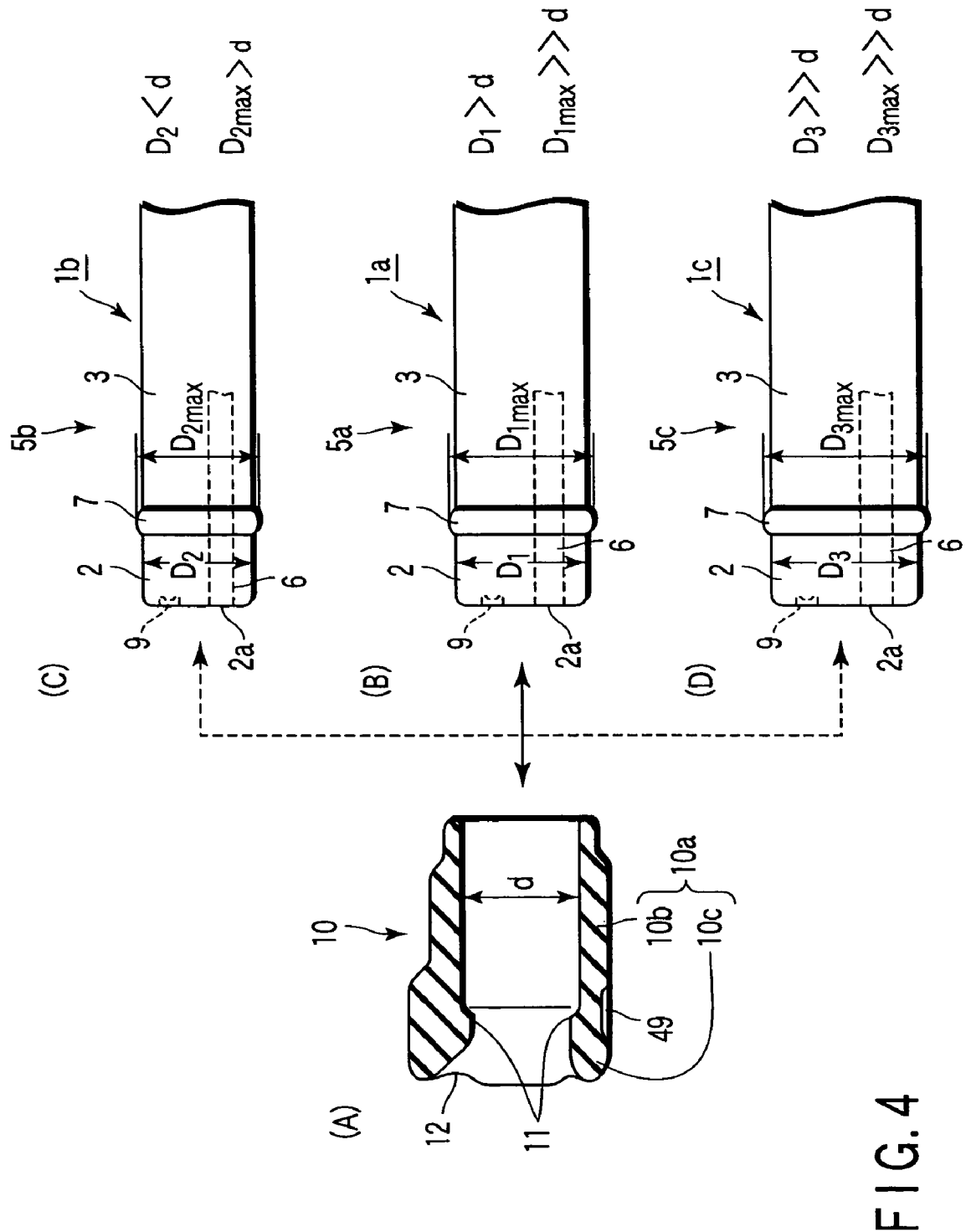
FIG. 4 is schematic view when the hood showing a cross section is attached to the endoscope insertion portion which shows a side face and has an appropriate outside diameter indicated by an arrow of a solid line relative to the endoscope hood according to the embodiment of the present invention having an arbitrary inside diameter, and when the hood showing a cross section is attached to the endoscope insertion portion which shows a side face and has each inappropriate different outside diameter indicated by each arrow of a broken line.

Moreover, as shown in (A) of FIG. 4, an index 49 is provided on the outer peripheral surface of the endoscope hood 10 in order to perform positioning and press fitting at a predetermined position of the distal end portion 2 of the endoscope insertion portion 5. In this embodiment, as to the index 49, a part of the outer periphery extending from the protrusion portion 10c of the hood main body 10a to the press fitting fixing portion 10b is formed as a concave portion. Preferably, the index 49 is colored in a color different from that of any other part of the hood main body 10a.

As shown in (B) of FIG. 4, the outside diameter of the distal end portion 2 of the endoscope insertion portion (first endoscope insertion portion) 5a of the first endoscope 1a is D1 which is appropriate to an inside diameter d of the fitting hole portion of the press fitting fixing portion 10b of the hood 10. This outside diameter D1 is slightly larger than the inside diameter d of the fitting hole portion of the press fitting fixing portion 10b of the hood 10. The outside diameter of the above-described first connection portion 7 is D1max. This outside diameter D1max is slightly larger than the outside diameter D1 of the distal end portion 2 (D1>d, D1max>d).

As shown in (C) of FIG. 4, an outside diameter of the distal end portion 2 of the endoscope insertion portion (second endoscope insertion portion) 5b of a second endoscope 1b is, e.g., D2. This outside diameter D2 is equal to or slightly smaller than the inside diameter d of the fitting hole portion of the press fitting fixing portion 10b of the hood 10. An outside diameter of the first connection portion 7 is D2max. This outside diameter D2max is slightly larger than the inside diameter d of the fitting hole portion of the press fitting fixing portion 10b of the hood 10 (D2<d, D2max>d).

As shown in (D) of FIG. 4, an outside diameter of the distal end portion 2 of the endoscope insertion portion (third endoscope insertion portion) 5c of a third endoscope 1c is, e.g., D3. This outside diameter D3 is larger than the outside diameter D1 of the distal end portion 2 of the first endoscope insertion portion 5a. An outside diameter of the first connection portion 7 is D3max. This outside diameter D3max is larger than the outside diameter D3 of the distal end portion 2 of the insertion portion 5c (D3>d, D3max>d).

Figure 5A:
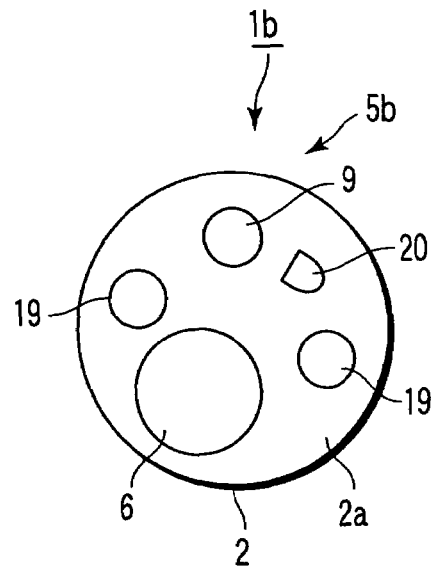
FIGS. 5A and 5B are front views showing the distal end portions of the endoscope insertion portions having different inappropriate outside diameters indicated by the arrows of the broken lines depicted in FIG. 4.
Figure 5B:
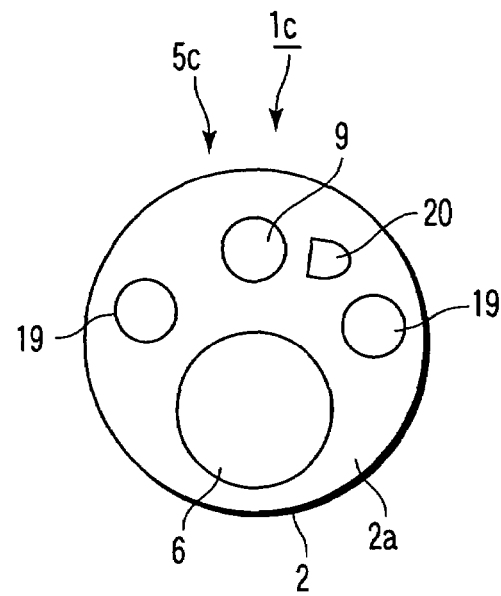

FIGS. 5A and 5B show layouts of respective constituent elements on the end surfaces 2a of the distal end portions 2 of the endoscope insertion portions 5b and 5c of the second and third endoscopes 1b and 1c, respectively.

As shown in FIG. 5A, an opening portion of the endotherapy accessory channel 6 which is generally the largest element on the distal end surface 2a is provided on the distal end surface 2a of the distal end portion 2 of the endoscope insertion portion 5b of the second endoscope 1b so as to be biased on the rather lower side away from the center of the distal end surface 2a and on the rather left side. In this embodiment, a pair of illumination lenses 19 and a circular object lens 9 are provided on this distal end surface 2a. In FIG. 5A, the illumination lenses 19 are provided in the right-and-left direction with respect to the center of the distal end surface 2a, and one of them is arranged on the upper left side of the endotherapy accessory channel 6 and the other one is arranged on the right side. The object lens 9 is arranged on the rather upper side relative to the center. An air supply/water supply nozzle 20 is caused to protrude on the distal end surface 2a (not shown in FIG. 1).

It is to be noted that the maximum field angle A1 in the opposite side direction of this second endoscope 1b shown in FIG. 1 is assumed to be, e.g., 140°. It is assumed that a distance between the center of the object lens 9 and an outer peripheral portion of the distal end portion 2 is, e.g., 2.8 mm.

As shown in FIG. 5B, the opening portion of the endotherapy accessory channel 6 which is generally the most largest element on this distal end surface 2a is provided on the distal end surface 2a of the distal end portion 2 of the endoscope insertion portion 5c of the third endoscope 1c on the rather lower side away from the center of the distal end surface 2a. A pair of illumination lenses 19 and a circular object lens 9 are provided on this distal end surface 2a. The illumination lenses 19 are arranged in the right-and-left direction relative to the center of the distal end surface 2a and on the rather upper side away from the endo-therapy accessory channel 6 in FIG. 5B. The object lens 9 is arranged on the rather upper side with respect to the center. An air supply/water supply nozzle 20 is caused to protrude on the distal end surface 2a (not shown in FIG. 1).

It is to be noted that the maximum field angle A1 in the opposite side direction of the third endoscope 1c shown in FIG. 1 is assumed to be, e.g., 170°. It is assumed that a distance between the center of the object lens 9 and an outer peripheral portion of the distal end portion 2 is, e.g., 3.6 mm.

Like the index 49 provided at the outer peripheral portion of the hood main body 10a mentioned above, it is preferable to color the distal end portions 2 of the insertion portions 5a, 5b and 5c of the first to third endoscopes 1a, 1b and 1c, or form an index (not shown) having an irregular shape to each of the distal end portions 2.

Description will now be given as to the effect when the hood 10 formed for the first endoscope 1a is attached to the distal end portions 2 of the respective endoscope insertion portions 5a, 5b and 5c of such first to third endoscopes 1a, 1b and 1c.

As shown in (A) and (B) of FIG. 4, the index 49 on the outer periphery of the hood 10 and the index (not shown) provided to the distal end portion 2 of the insertion portion 5a of the first endoscope 1a are positioned, and the hood 10 is then attached by press fitting. That is, the hood 10 is attached in a predetermined direction at a predetermined position of the distal end portion 2 of the insertion portion 5a of the first endoscope 1a. At this moment, the impingement end portion 11 of the hood 10 is press-fitted until it comes into contact with the distal end surface 2a of the distal end portion 2 of the insertion portion 5a of the first endoscope 1a.

Pressures applied to the outer peripheral portion of the distal end portion 2 of the insertion portion 5a of the first endoscope 1a and to the first connection portion 7 between this distal end portion 2 and the bending portion 3 by attachment of the hood 10 become substantially uniform. At this time, the protrusion portion 10c of the hood 10 is not displayed in the observation image display portion 14 of the monitor device 13 shown in FIG. 3.

Subsequently, as shown in (A) and (C) of FIG. 4, like the first endoscope 1a, the index 49 of the hood 10 and the index (not shown) provided to the distal end portion 2 of the insertion portion 5b of the second endoscope 1b are positioned, and the hood 10 is then attached in the case of the second endoscope 1b. That is, the hood 10 is attached in a predetermined direction at a predetermined position of the distal end portion 2 of the insertion portion 5b of the second endoscope 1b. Attachment continues until the impingement end portion 11 of the hood 10 comes into contact with the distal end surface 2a of the distal end portion 2 of the insertion portion 5b of the second endoscope 1b.

At this moment, the inner peripheral surface of the press fitting fixing portion 10b of the hood main body 10a is brought into contact (press fitted) with only the first connection portion 7 between the distal end portion 2 of the insertion portion 5b and the bending portion 3. Therefore, the contact of the hood 10 to the distal end portion 2 of the insertion portion 5b of the second endoscope 1b is lower than the contact of the same to the distal end portion 2 of the insertion portion 5a of the first endoscope 1a.

Figure 6:
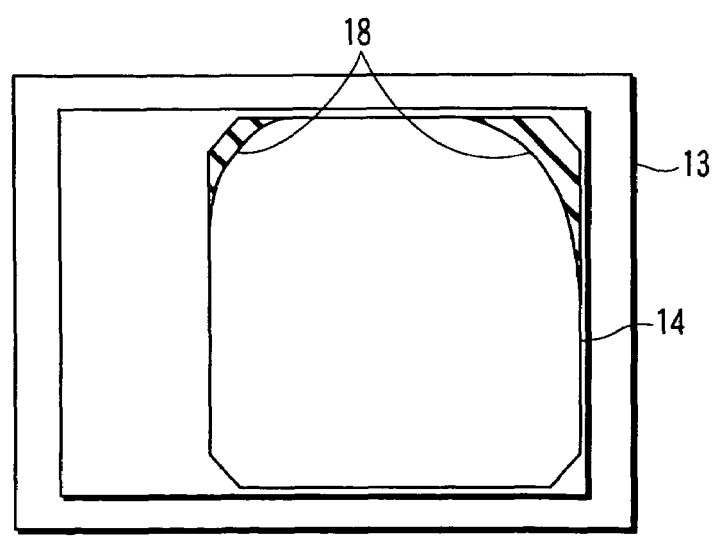
FIG. 6 is a schematic view of an observation image monitor device showing a state that an edge portion of a protrusion portion of the hood is shown in an observation image display portion when observing from the distal end portion of the endoscope insertion portion having the hood according to the embodiment of the present invention attached thereto by using an object lens.

Compared with the first endoscope 1a, a difference in distance between the center of the object lens 9 and the outer peripheral portion of the distal end portion 2 is 0.4 mm (=3.2 mm−2.8 mm). Therefore, a part 18 of the outer edge of the protrusion portion 10c is displayed in the observation image display portion 14 of the monitor device 13 shown in FIG. 6. That is, an area in which the outer edge portion of the protrusion portion 10c is displayed is increased as compared with an appropriate attachment state like a state that the hood 10 is attached to the first endoscope 1a. As described above, when the hood 10 is attached in an inappropriate attachment state, an area in which the protrusion portion 10c is displayed is increased in an observation image. Therefore, the protrusion portion 10c functions as attachment state confirming means which causes a recognition of a state that an inappropriate attachment occurs at the distal end portion 2 of the insertion portion 5b of the second endoscope 1b and gives a warning.

Here, an operator visually recognizes the observation image display portion 14 of the monitor device 13, and judges whether the protrusion portion 10c of the hood 10 is displayed. When the hood 10 is appropriately attached to the first endoscope 1 having a proper outside diameter like when the hood 10 is attached to the first endoscope 1a and the protrusion portion 10c is not displayed, the first endoscope 1b may be used as it is. When the part 18 of the outer edge of the protrusion portion 10c is displayed somewhat (see FIG. 6) like when the hood 10 is attached to the second endoscope 1b and it is hard to make a judgment, a judgment (determination) is made by, e.g., the following hood propriety judgment device.

The hood propriety judging device previously sets an allowable range that the protrusion portion 10c is displayed in the observation image display portion 14 by the image-processing device. Then, the distal end portion 2a of the insertion portion 5b of the endoscope 1b is brought into contact with a member having a uniform color different from a color of the hood. An observation image displayed in the observation image display portion 14 of the monitor device 13 is subjected to binarization processing in the image-processing device, and an area ratio of the protrusion portion 10c displayed in the observation image display portion 14 is calculated. Based on the calculated area ratio, a judgment is made upon whether the hood 10 is appropriately attached to the second endoscope 1b.

It is to be noted that, when the area ratio the displayed protrusion portion 10c is larger than a set value, a sound (buzzer) or a flashing light is used to notify the fact that the hood 10 is not appropriate for the second endoscope 1b.

As shown in (A) and (D) of FIG. 4, like the first endoscope 1a, the index 49 of the hood 10 and the index (not shown) provided to the distal end portion 2 of the insertion portion 5c of the third endoscope 1c are positioned, and then the hood 10 is attached by press fitting in the case of the third endoscope 1c. That is, the hood 10 is attached in a predetermined direction at a predetermined position of the distal end portion 2 of the insertion portion 5c of the third endoscope 1c. Attachment continues until the impingement end portion 11 of the hood 10 comes into contact with the distal end surface 2a of the distal end portion 2 of the insertion portion 5c of the third endoscope 1c. The inner peripheral surface of the hood 10 is deformed up to nearly the limit of elastic deformation and brought into contact with the outer peripheral portion of the distal end portion 2 of the insertion portion 5c and the first connection portion 7. The hood 10 is elastically deformed in a direction that the protrusion portion 10c shrinks on the inner side, and the press fitting fixing portion 10b comes into contact with the vicinity of the above-described boundary and the first connection portion 7. Therefore, the pressure welding force is hardly transmitted to the outer peripheral surface of the distal end portion 2. Alternatively, the hood main body 10a is attached to the outer peripheral surface of the distal end portion 2 and the first connection portion 7 by the firm press fitting force.

Compared with the first endoscope 1a, a difference in the maximum field angle A1 in the opposite side direction between the first endoscope 1a and the third endoscope 1c is 30° (=170°−140°). Therefore, a part 18 of the outer edge of the protrusion portion 10c is displayed in the observation image display portion 14 of the monitor device 13 shown in FIG. 6. That is, compared with an appropriate attachment state like a state that the hood 10 is attached to the first endoscope 1a, an area in which the protrusion portion 10c is displayed is increased. Therefore, the protrusion portion 10c functions as attachment state confirming means which notifies the fact that an inappropriate attachment state occurs at the distal end portion 2 of the insertion portion 5c of the third endoscope 1c and gives a warning.

Thereafter, like the case that the hood 10 is attached to the second endoscope 1b, a judgment is made upon whether the hood 10 is appropriate for the third endoscope 1c.

Therefore, in the case of the distal end portion 2 of the first endoscope insertion portion 5a having the outside diameter which falls within the allowable range with respect to this hood 10, the protrusion portion 10c is not displayed in the screen even if the object lens 9 is set to the maximum field angle A1. In the case of the distal end portions 2 of the second and third endoscope insertion portions 5b and 5c having the outside diameters which are out of the allowable range with respect to this hood 10, the outer edge portion of the protrusion portion 10c is displayed in the screen when the object lens 9 is set to the maximum field angle A1. It is possible to readily recognize whether the hood 10 is attached to the distal end portion 2 of the first endoscope insertion portion 5a having the appropriate outside diameter.

Incidentally, in this embodiment, a description has been given as to the fact that the outer edge portion of the protrusion portion 10c is not displayed in the observation image display portion 14 when the hood 10 is attached to the distal end portion 2 of the first endoscope insertion portion 5a having an appropriate outside diameter, but the protrusion portion 10c of the hood 10 may be formed in such a manner that the outer edge portion of the protrusion portion 10c is displayed at the outer edge of the observation image display portion 14 to some degree.

Additionally, the values such as a length of the distance or the maximum field angle A1 described above are just examples, and any other values may be adopted as long as the protrusion portion 10c satisfying various kids of conditions is formed.

Further, in this embodiment, attachment is carried out with an optimum position between the hood 10 and the distal end portion 2 of the endoscope insertion portion 5 by using the index 49. Further, as shown in FIG. 7A, attachment may be effected with an optimum position between the hood 10 and the distal end portion 2 of the endoscope insertion portion 5 by using a positioning member 15.

Figure 7A:
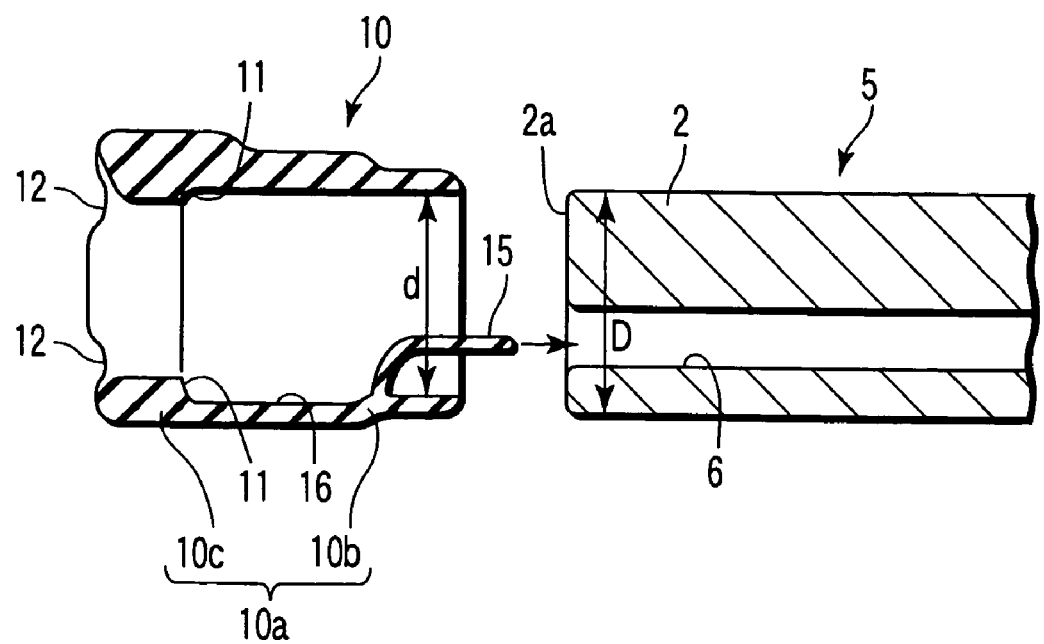
FIG. 7A is a schematic partial cross-sectional view showing a state that a positioning member of the hood according to the embodiment of the present invention is opposed to an endo-therapy accessory channel of the endoscope insertion portion.

As shown in FIG. 7A, a tab-shaped positioning member 15 is integrally formed on the inner peripheral surface of the press fitting fixing portion 10b of the hood main body 10a. This positioning member 15 is further extended to the rear side from the proximal end portion of the press fitting fixing portion 10b and caused to protrude. On the inner peripheral surface of the press fitting fixing portion 10b is formed a concave portion 16 in which the positioning member 15 is accommodated when the hood 10 is attached to the distal end portion 2 of the insertion portion 5 of the endoscope 1. This positioning member 15 has a length such that this member does not come into contact with the inner peripheral surface of the protrusion portion 10c on the front side away from the impingement end portion 11 even when a proximal end portion of this positioning member 15 is bent.

Furthermore, for example, the tab-shaped positioning member 15 which is integral with the hood main body 10a provided in the vicinity of the rear end portion of the hood 10 is arranged in, e.g., the endotherapy accessory channel 6.

Figure 7B:
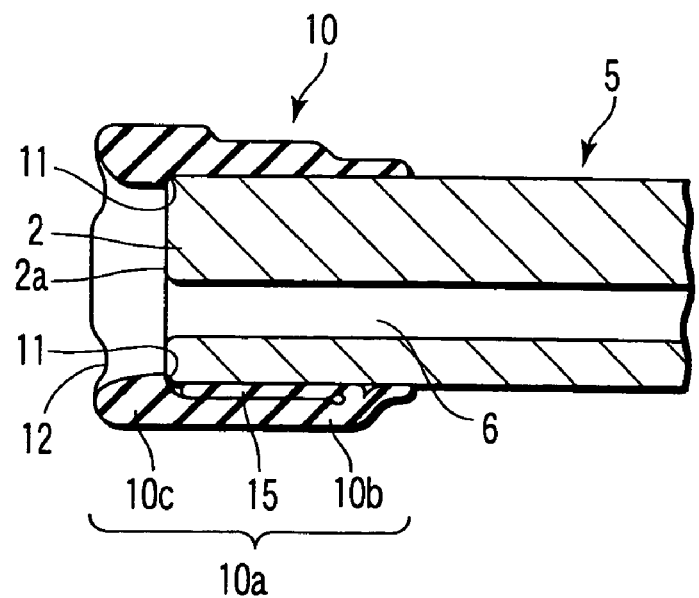
FIG. 7B is a schematic partial cross-sectional view showing a state that the hood is attached to the distal end portion of the endoscope insertion portion by using the positioning member of the hood depicted in FIG. 7A.

As shown in FIG. 7B, when the press fitting fixing portion 10b is press-fitted to the distal end portion 2 of the insertion portion 5 of the endoscope 1 from a state that the positioning member 15 depicted in FIG. 7A is opposed to the endotherapy accessory channel 6, the positioning member 15 once enters the endo-therapy accessory channel 6. Thereafter, as the press fitting fixing portion 10b is press-fitted, the positioning member 15 is removed at a part between the opening portion of the channel 6 and the edge portion of the distal end surface 2a while being bent from the base portion thereof. The positioning member 15 is bent at the base portion thereof, and elastically deformed and accommodated between the distal end portion 2 and the concave portion 16 at the inner peripheral portion of the press fitting fixing portion 10b.

By doing so, the hood 10 can be further assuredly attached at a predetermined position with respect to the circumferential direction of the distal end portion 2 of the endoscope insertion portion 5.

It is to be noted that the positioning member 15 may be automatically cut out at the time of press fitting attachment.

Although the embodiment has been concretely described with reference to the accompanying drawings, the present invention is not restricted to the foregoing embodiment, and it includes all embodiments carried out without departing from the scope of the invention.

What is claimed is:

1. An endoscope hood comprising:
a cylindrical attachment portion configured to be attached to a distal end portion of an insertion portion of a first endoscope and to be attached to a distal end portion of an insertion portion of a second endoscope having an outside diameter fitting for the attachment, the outside diameter being different from an outside diameter of the distal end portion of the insertion portion of the first endoscope;
a protrusion portion formed on an end side of the cylindrical attachment portion, the protrusion portion configured to protrude in an observation visual field direction from the distal end portion of the insertion portion of at least the second endoscope, and having an area displayed in an observation image of the second endoscope that is larger than an area displayed in an observation image of the first endoscope,
wherein the protrusion portion is formed into a shape such that the protrusion portion is not visible in an observation image of the first endoscope when the attachment portion is attached to the distal end portion of the first endoscope insertion portion, and such that the protrusion portion appears in an observation image of the second endoscope when the attachment portion is attached to the distal end portion of the second endoscope insertion portion; and
a positioning member configured to enable attachment at positions appropriate to the first and second endoscopes provided on an inner peripheral surface of the attachment portion.

2. The endoscope hood according to claim 1, wherein an outside diameter of the distal end portion of the insertion portion of the second endoscope is smaller than an outside diameter of the distal end portion of the insertion portion of the first endoscope.

3. The endoscope hood according to claim 2, wherein the attachment portion has elasticity such that the attachment portion is deformed at least in a radial direction in such a manner that the attachment portion is operable to be attached by press fitting.

4. The endoscope hood according to claim 1, wherein an outside diameter of the distal end portion of the insertion portion of the second endoscope is larger than an outside diameter of the distal end portion of the insertion portion of the first endoscope.

5. The endoscope hood according to claim 4, wherein the attachment portion has elasticity such that the attachment portion is deformed at least in a radial direction in such a manner that the attachment portion is operable to be attached by press fitting.

6. The endoscope hood according to claim 1, wherein the protrusion portion has a concave portion matched with a visual field area observed by the first endoscope.

7. The endoscope hood according to claim 6, wherein the attachment portion has elasticity such that the attachment portion is deformed at least in a radial direction in such a manner that the attachment portion is operable to be attached by press fitting.

8. The endoscope hood according to claim 1, wherein the positioning member is integrally formed on the inner peripheral surface of the attachment portion.

9. The endoscope hood according to claim 8, wherein the attachment portion has elasticity such that the attachment portion is deformed at least in a radial direction in such a manner that the attachment portion is operable to be attached by press fitting.

10. The endoscope hood according to claim 1, wherein the attachment portion has elasticity such that the attachment portion is deformed at least in a radial direction in such a manner that the attachment portion is operable to be attached by press fitting.

11. The endoscope hood according to claim 1, wherein the attachment portion has elasticity such that the attachment portion is deformed at least in a radial direction in such a manner that the attachment portion is operable to be attached by press fitting.

12. An endoscope hood comprising:
- a cylindrical attachment portion configured to be attached to a distal end portion of an insertion portion of a first endoscope and to be attached to a distal end portion of an insertion portion of a second endoscope having an outside diameter fitting for the attachment, the outside diameter being different from an outside diameter of the distal end portion of the insertion portion of the first endoscope;
- a protrusion portion formed on an end side of the cylindrical attachment portion, the protrusion portion configured to protrude in an observation visual field direction from the distal end portion of the insertion portion of at least the second endoscope, and having an area displayed in an observation image of the second endoscope that is larger than an area displayed in an observation image of the first endoscope; and
- a positioning member configured to enable attachment at positions appropriate to the first and second endoscopes provided on an inner peripheral surface of the attachment portion.

13. The endoscope hood according to claim 12, wherein the protrusion portion is formed into a shape such that the protrusion portion is not visible in an observation image of the first endoscope when the attachment portion is attached to the distal end portion of the first endoscope insertion portion, and such that the protrusion portion appears in an observation image of the second endoscope when the attachment portion is attached to the distal end portion of the second endoscope insertion portion.

14. The endoscope hood according to claim 12, wherein an outside diameter of the distal end portion of the insertion portion of the second endoscope is smaller than an outside diameter of the distal end portion of the insertion portion of the first endoscope.

15. The endoscope hood according to claim 14, wherein the attachment portion has elasticity such that the attachment portion is deformed at least in a radial direction in such a manner that the attachment portion is operable to be attached by press fitting.

16. The endoscope hood according to claim 12, wherein an outside diameter of the distal end portion of the insertion portion of the second endoscope is larger than an outside diameter of the distal end portion of the insertion portion of the first endoscope.

17. The endoscope hood according to claim 16, wherein the attachment portion has elasticity such that the attachment portion is deformed at least in a radial direction in such a manner that the attachment portion is operable to be attached by press fitting.

18. The endoscope hood according to claim 12, wherein the protrusion portion has a concave portion matched with a visual field area observed by the first endoscope.

19. The endoscope hood according to claim 18, wherein the attachment portion has elasticity such that the attachment portion is deformed at least in a radial direction in such a manner that the attachment portion is operable to be attached by press fitting.

20. The endoscope hood according to claim 12, wherein the positioning member is integrally formed on the inner peripheral surface of the attachment portion.

21. The endoscope hood according to claim 20, wherein the attachment portion has elasticity such that the attachment portion is deformed at least in a radial direction in such a manner that the attachment portion is operable to be attached by press fitting.

22. The endoscope hood according to claim 12, wherein the attachment portion has elasticity such that the attachment portion is deformed at least in a radial direction in such a manner that the attachment portion is operable to be attached by press fitting.

23. The endoscope hood according to claim 12, wherein the attachment portion has elasticity such that the attachment portion is deformed at least in a radial direction in such a manner that the attachment portion is operable to be attached by press fitting.

* * * * *